US00PP31625P2

(12) United States Plant Patent
Snijder

(10) Patent No.: US PP31,625 P2
(45) Date of Patent: Mar. 31, 2020

(54) ***PELARGONIUM* PLANT NAMED 'PEQZ0069'**

(50) Latin Name: *Pelargonium peltatum*
Varietal Denomination: PEQZ0069

(71) Applicant: SYNGENTA PARTICIPATIONS AG, Basel (CH)

(72) Inventor: Ronald Christiaan Snijder, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 16/350,877

(22) Filed: Jan. 28, 2019

(51) Int. Cl.
*A01H 5/02* (2018.01)
*A01H 6/42* (2018.01)

(52) U.S. Cl.
USPC ..... Plt./326
CPC ..... *A01H 6/425* (2018.05)

(58) Field of Classification Search
USPC ..... Plt./326
See application file for complete search history.

*Primary Examiner* — Anne Marie Grunberg
(74) *Attorney, Agent, or Firm* — Dale Skalla

(57) ABSTRACT

A new *Pelargonium* plant named 'PEQZ0069' particularly distinguished by white colored inflorescences that slowly fade to light pink with large double florets held above medium-green foliage on a trailing and well branched plant habit.

2 Drawing Sheets

Latin name of the genus and species of the plant claimed: *Pelargonium peltatum*.

Varietal denomination: 'PEQZ0069'.

BACKGROUND OF THE NEW PLANT

The present invention comprises a new *Pelargonium*, botanically known as *Pelargonium peltatum*, and hereinafter referred to by the variety name 'PEQZ0069'.

'PEQZ0069' is a product of a planned breeding program. The new cultivar 'PEQZ0069' has white colored inflorescences that slowly fade to light pink with large double florets held above medium-green foliage on a trailing and well branched plant habit.

'PEQZ0069' originates from a hybridization in a controlled breeding program made in February 2012, in a greenhouse in Amatitlán, Guatemala. The female parent was a patented plant 'HWD Onyx', (described in U.S. Pat. No. 9,756) with a more compact plant habit when compared to 'PEQZ0069'.

The male parent of 'PEQZ0069' was an unpatented, proprietary plant of *P. peltatum* parentage, identified as 'PEL-095032-01' with more salmon colored florets and a more open plant habit when compared to 'PEQZ0069'. The resultant seed was sown in December 2012.

'PEQZ0069' was selected as one flowering plant within the progeny of the stated cross in April 2013 in a greenhouse in Enkhuizen, The Netherlands.

The first act of asexual reproduction of 'PEQZ0069' was accomplished when vegetative cuttings were propagated from the initial selection in the May 2013 in a greenhouse in Enkhuizen, The Netherlands.

BRIEF SUMMARY OF INVENTION

Horticultural examination of plants grown from cuttings of the plant initiated in June 2013 in Enkhuizen, The Netherlands, and continuing thereafter, has demonstrated that the combination of characteristics as herein disclosed for 'PEQZ0069' are firmly fixed and are retained through successive generations of asexual reproduction.

'PEQZ0069' has not been observed under all possible environmental conditions. The phenotype may vary significantly with variations in environment such as temperature, light intensity, and day length.

A Plant Breeder's Right for this cultivar has not yet been applied for. 'PEQZ0069' has not been made publicly available prior to the effective filing date of this application, notwithstanding any disclosure that may have been made less than one year prior to the effective filing date of this application by the inventor or another who obtained 'PEQZ0069' directly from the inventor.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

The accompanying photographic drawings show typical flower and foliage characteristics of 'PEQZ0069' with colors being as true as possible with an illustration of this type.

Figure 1:
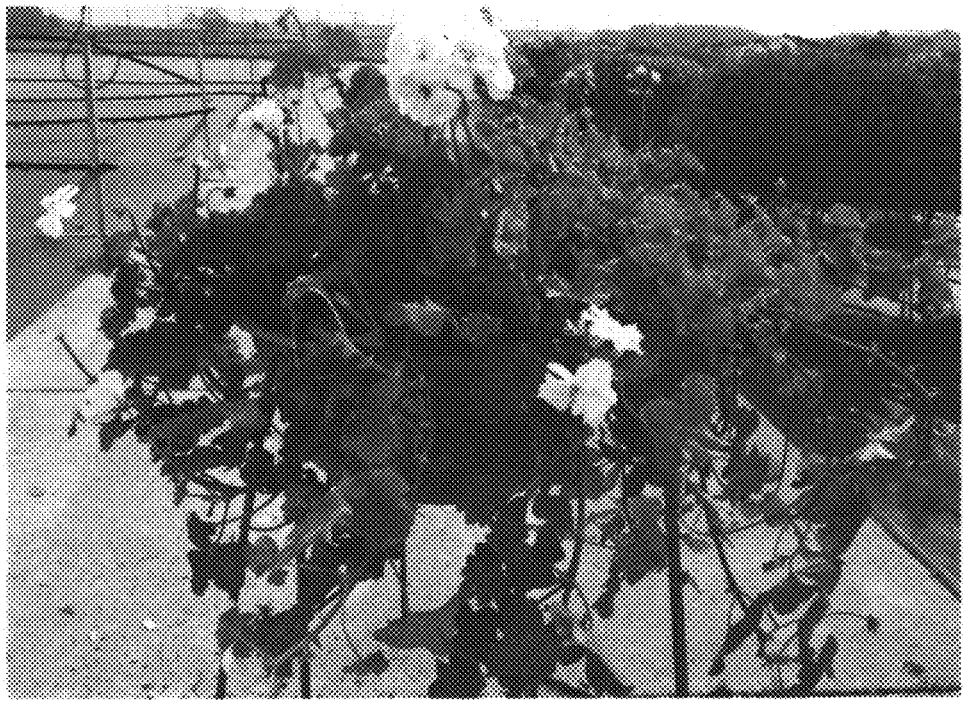
Figure 2:
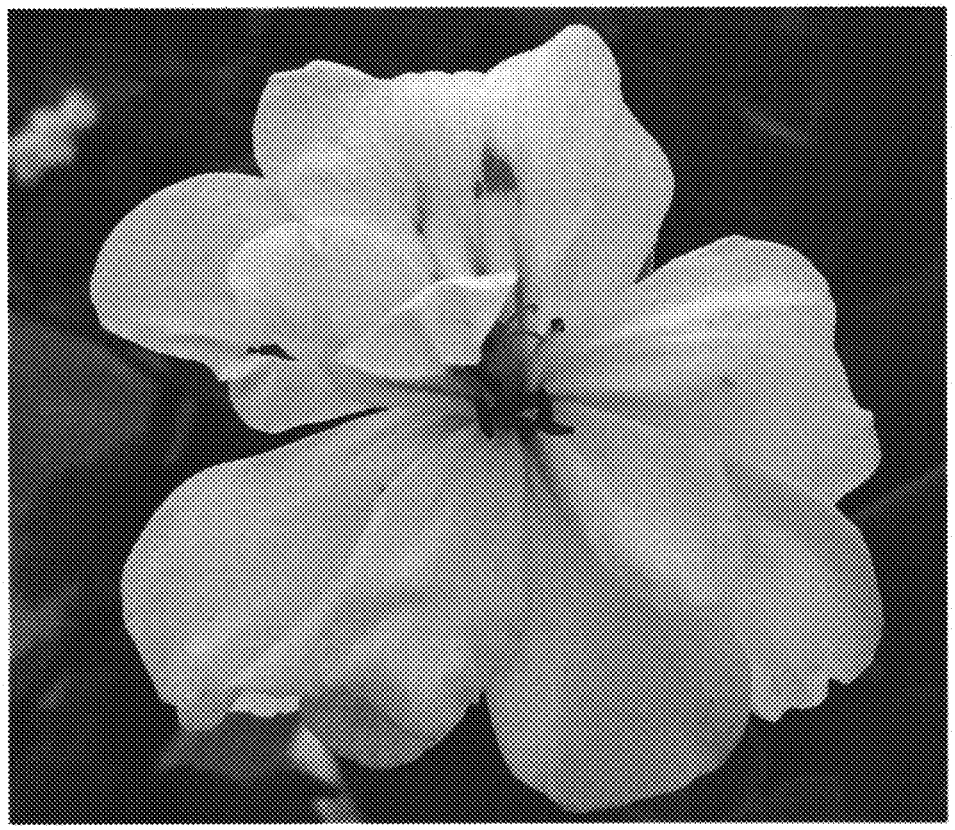
Figure 3:
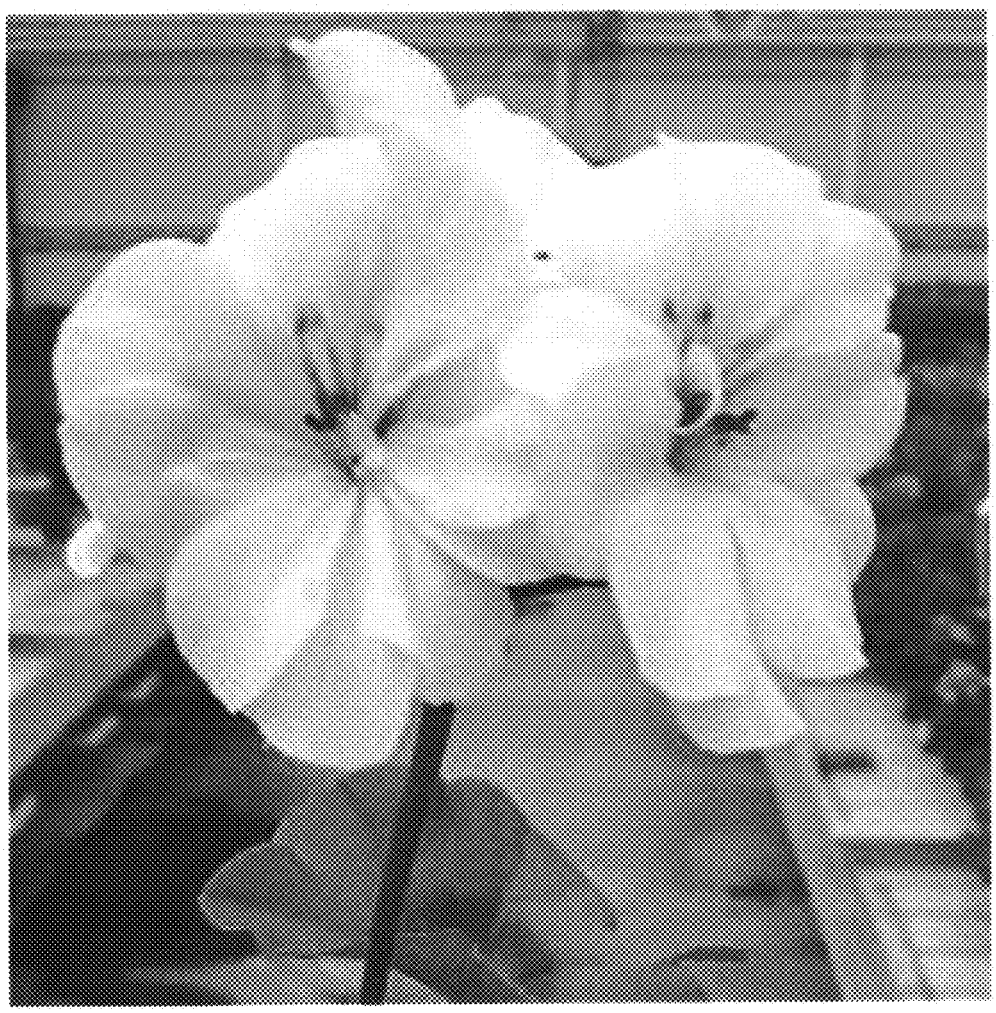

The photographic drawing in FIG. 1, shows a basket with 4 flowering plants of the new variety, FIG. 2, a close-up of a ripe flower that has faded to pink, and FIG. 3, a close-up of a fully expanded, still white floret.

DETAILED BOTANICAL DESCRIPTION

The plant descriptions and measurements were taken in Andijk, The Netherlands in September under natural light. These plants were approximately 13 weeks old and were grown in a 1 gallon pots, in a greenhouse trial. The plants shown in the photographs were about 25 weeks old growing in a 10 inch pot in a greenhouse. The photographs were taken in October 2018.

Color references are made to The Royal Horticultural Society Colour Chart (R.H.S.) 2001.

TABLE 1

DIFFERENCES BETWEEN THE NEW VARIETY 'PEQZ0069' AND A MOST SIMILAR VARIETY

| | 'PEQZ0069' | 'Filun' (U.S. Plant Pat. No. 16,643) |
|---|---|---|
| Floret shape: | Ovate florets, with petals overlapping | Oval-obovate florets, some petals not overlapping sometimes free or with space between the petals |
| Floret petal color: | White, slowly fading to pink | White or very light pink |

Plant:
- *Form, growth and habit.*—Semi-upright to trailing.
- *Plant height.*—18-22 cm.
- *Plant height (inflorescence included).*—22-26 cm.
- *Plant width.*—35-40 cm.

Roots:
- *Number of days to initiate roots.*—15-18 days at about 22 degrees C.
- *Number of days to produce a rooted cutting.*—21-23 days at 22 degrees C.
- *Type.*—Fine, fibrous, free branching.
- *Color.*—RHS N155B but whiter.

Foliage:
- *Immature leaf, color upper surface.*—Between RHS 137B/C and RHS 144A.
- *Immature leaf, lower surface.*—Between RHS 138B and RHS 144A.
- *Mature leaf, color upper surface.*—Between RHS 137A/B and RHS 144A.
- *Mature leaf, color lower surface.*—Between RHS 138B and RHS 144A.
- *Length.*—4.0-4.5 cm.
- *Width.*—7.0-8.0 cm.
- *Shape.*—Orbicular.
- *Base shape.*—Cordate, heart-shaped.
- *Apex shape.*—Rounded, waved.
- *Margin.*—Wavy, undulate margins.
- *Texture upper side.*—Pilose.
- *Texture lower side.*—Pilose.
- *Leaf zonation color.*—Closest to RHS 202A.
- *Color of veins, upper surface.*—Closest to RHS 144A, becoming indistinct.
- *Color of veins, lower surface.*—Closest to RHS 144A, becoming indistinct.
- *Pattern of veining.*—Palmate.
- *Petiole color.*—Closest to RHS 144A.
- *Petiole length.*—2.5-5.5 cm.
- *Diameter of petiole.*—About 2 cm.
- *Texture.*—Pilose, hirsute hairs.

Stem:
- *Quantity of branches.*—8-10 branches extending from base (lateral branches not included in counting).
- *Color of stem/branches.*—Closest to RHS 144A.
- *Length of stem/branches.*—25-55 cm.
- *Diameter.*—0.7-0.8 cm.
- *Length of internodes.*—1.5-7.0 cm.
- *Texture.*—Hirsute, pilose hairs.

Peduncle:
- *Color of peduncle.*—Closest to RHS 144A.
- *Length of peduncle.*—8.0-20.0 cm.
- *Peduncle diameter.*—0.3-0.4 cm.
- *Texture.*—Hirsute.

Pedicel:
- *Color of pedicel.*—Closest to RHS 144A.
- *Length of pedicel.*—2.0-2.5 cm.
- *Diameter of pedicel.*—0.15-0.2 cm.
- *Texture.*—Pilose.

Bud (just before opening):
- *Color.*—White, margins edged with a touch of pink.
- *Length.*—About 2.0 cm.
- *Width.*—About 1.0 cm.
- *Shape.*—Elliptical.

Inflorescence:
- *Type.*—Umbel, semi-spherical.
- *Lastingness of individual flowers.*—7-9 days at 18° C. temperature.
- *Number of inflorescences per plant.*—7 mature and 8 immature umbels in various stages.
- *Fragrance.*—None.
- *Umbel diameter.*—About 8.0-10.0 cm.
- *Umbel depth.*—About 4.0-5.0 cm.

Corolla:
- *Form.*—Semi-double.
- *Number of petals.*—11-18.
- *Diameter of flower.*—4.5-5.0 cm.
- *Depth of flower.*—1.5-2.0 cm.
- *Color upper petals, upper surface.*—White RHS 155C, fading slowly to light pink which is close to RHS 56A. Distinct pink marking (stripes and dots) from base to middle. Color of marking closest to RHS 66A.
- *Color upper petals, lower surface.*—White.
- *Length of upper petals.*—2.7-3.0 cm.
- *Width of upper petals.*—1.5-1.7 cm.
- *Color lower petals, upper surface.*—White.
- *Color lower petals, lower surface.*—White.
- *Length of lower petals.*—2.5-3.2 cm.
- *Width of lower petals.*—1.7-1.9 cm.
- *Petal shape.*—Obovate.
- *Apex shape.*—Rounded.
- *Margin.*—Entire.
- *Base.*—Attenuate.
- *Petal texture.*—Papilosse.

Calyx:
- *Number of sepals.*—5.
- *Color of sepals.*—Closest to RHS 144A.
- *Length of sepals.*—1.0-1.5 cm.
- *Width of sepals.*—1.3-1.5 cm.
- *Sepal shape.*—Lanceolate to enciform.
- *Apex shape.*—Acute.
- *Margins.*—Entire.
- *Texture, upper surface.*—Pilose.
- *Texture, lower surface.*—Pilose.

Reproductive organs:

Gynoecium:
- *Pistil.*—1.
- *Length.*—1.0-1.1 cm.
- *Style color.*—Closest to RHS 145D (base), apex: closest to RHS 66A.
- *Style length.*—0.5-0.6 cm.
- *Stigma color.*—Closest to RHS 66A.
- *Ovary color.*—Closest to RHS 145A.
- *Ovary length.*—0.4-0.5 cm.
- *Ovary diameter.*—About 0.3 cm.

Androecium:

*Number of stamens*.—6-8.

*Color of filaments*.—Base: Closest to RHS 145D; apex closest to: RHS 55C.

*Length filaments*.—1.0-1.2 cm.

*Anther color*.—Closest to RHS 187D.

*Length of anthers*.—About 0.2-0.3 cm.

*Color of pollen*.—Not detected.

*Pollen amount*.—None.

*Fertility/seed set*.—Has not been determined to date.

*Disease/pest resistance*.—Has not been determined to date.

What is claimed is:

1. A new and distinct variety of *Pelargonium* plant named 'PEQZ0069' substantially as illustrated and described herein.

* * * * *